United States Patent
Kawanishi et al.

(10) Patent No.: US 6,818,190 B2
(45) Date of Patent: Nov. 16, 2004

(54) APPARATUS FOR PREPARING NON-PHOTOSENSITIVE FATTY ACID SILVER SALT GRAINS

(75) Inventors: Naoyuki Kawanishi, Kanagawa (JP); Takashi Ando, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 162 days.

(21) Appl. No.: 10/217,517

(22) Filed: Aug. 14, 2002

(65) Prior Publication Data

US 2003/0023103 A1 Jan. 30, 2003

Related U.S. Application Data

(62) Division of application No. 09/617,836, filed on Jul. 17, 2000, now Pat. No. 6,472,546.

(30) Foreign Application Priority Data

Jul. 15, 1999 (JP) ........................................ 1999/202081

(51) Int. Cl.⁷ .............................. B01F 7/00; F28D 7/00; C11C 1/00
(52) U.S. Cl. ...................... 422/235; 422/198; 422/225; 422/234; 422/235; 554/74; 554/156; 554/158; 556/110; 556/114
(58) Field of Search ................................. 422/225, 229, 422/234, 235, 198; 554/74, 156, 158, 110, 114; 260/413 S, 414; 430/619, 620

(56) References Cited

U.S. PATENT DOCUMENTS

| 4,273,723 A | 6/1981 | Hayashi et al. |
| 5,891,616 A | 4/1999 | Gilliams et al. |
| 6,326,133 B1 * | 12/2001 | Hioki .......................... 430/567 |

FOREIGN PATENT DOCUMENTS

| EP | 0508006 A1 | 4/1992 |
| EP | 0803763 A1 | 10/1997 |
| EP | 0887701 A1 | 12/1998 |
| EP | 0902005 A2 | 3/1999 |
| EP | 0962812 A1 | 6/1999 |
| JP | 53-31611 | 3/1978 |

* cited by examiner

Primary Examiner—Alexa Doroshenk
(74) Attorney, Agent, or Firm—Sughrue Mion, PLLC

(57) ABSTRACT

An apparatus for preparing non-photosensitive fatty acid silver salt grains having a first feeding device for feeding a silver ion-containing solution, the solvent of which is water or a mixture of water and an organic solvent, to a closed mixing device; a second feeding device for feeding a solution of a fatty acid alkali metal salt, the solvent of which is water, an organic solvent, or a mixture of water and an organic solvent, to the closed mixing device; a third feeding device for feeding water, or a mixture of water and an organic solvent to the closed mixing device; and the closed mixing device for mixing matter fed from the first, second and third feeding devices, and discharging a liquid containing non-photosensitive fatty acid silver salt grains.

6 Claims, 4 Drawing Sheets

APPARATUS FOR PREPARING NON-PHOTOSENSITIVE FATTY ACID SILVER SALT GRAINS

This is a divisional of application Ser. No. 09/617,836 filed Jul. 17, 2000; now U.S. Pat. No. 6,472,546; the disclosure of which is incorporated herein by reference.

TECHNICAL FIELD

The present invention relates to a method for preparing non-photosensitive fatty acid silver salt grains used for composing a photothermographic material, and an apparatus for implementing the method.

RELATED ART

A strong need for reducing the volume of waste process solution has arisen in recent medical field from viewpoints of environmental preservation and space saving. Thus a technology related to a photosensitive photothermographic material for medical diagnosis and photographic purposes has been desired, the material being such that affording efficient light exposure with a laser image setter or laser imager, and providing a black image with high resolution and sharpness. Such photosensitive photothermographic material can provide the user with a more simple and environment-conscious image producing system using no solution-base process chemical.

The image producing method based on heat development is disclosed, for example, in U.S. Pat. Nos. 3,152,904 and 3,457,075 and "Thermally Processed Silver Systems" written by D. Morgan and B. Shely, Imaging Processes and Materials, Neblette's 8th ed., edited by Sturge, V. Walworth and A. Shepp, p.2, (1989).

Such photosensitive material contains an reducible non-photosensitive silver source (e.g., organic acid silver salt), a catalytic amount of photocatalyst (e.g., silver halide) and a reducing agent for silver, all of which being generally dispersed in an organic binder matrix. While the photosensitive material is stable at the room temperature, it will produce silver through a redox reaction between the reducible silver source (which serves as an oxidizing agent) and the reducing agent when heated to a high temperature (80° C. or above, for example) after light exposure. The redox reaction is promoted by a catalytic action of the latent image produced by the light exposure. That is, the silver generated by the reaction of the reducible silver within the exposed area provides a black spot, which makes a contrast with the non-exposed area and is recognizable as an image.

The silver source employed by such system generally refers to a silver salt of a fatty acid, and a variety of methods for producing thereof have been known. Examples of the methods include such that preparing an organic acid silver salt in a concomitant solution of water and water-insoluble solvent as disclosed for example in JP-A-49-93310 (the code "JP-A" as used herein means an "unexamined published Japanese patent application"), JP-A-49-94619 and JP-A-53-68702; such that preparing an organic acid silver salt in an aqueous solution as disclosed in JP-A-53-31611, JP-A-54-4117 and JP-A-54-46709; and such that preparing an organic acid silver salt in an organic solvent as disclosed in JP-A-57-186745, JP-A-47-9432 and U.S. Pat. No. 3,700,458. In principle, the organic acid silver salt is obtained by dissolving a fatty acid into water under heating to a temperature of the melting point thereof or above, adding sodium hydroxide or an alkali metal salt under vigorous stirring, and further adding silver nitrate to convert an alkali soap into a silver soap.

The alkali soap forms micell in the aqueous solution, which appears as a milky liquid. The conversion reaction from such micellar state to silver salt, however, often suffers from a problem in production stability. Thus as a measure for obtaining a homogeneous solution of alkali soap, use of a mixed solution of water and alcohol as a solvent is disclosed in JP-A-55-40607.

Now the alkali soap shows alkalinity as its name suggests, and is prepared under a high pH environment. Adding silver nitrate to an alkali solution, however, not only produces silver oxide as a by-product but also results in an undesirable production of silver nucleus by an action of a trace amount of contaminant which inevitably generates during the production and exhibits a high reducing activity under such high-pH environment. Such by-product is quite disadvantageous in that degrading property of the photothermographic material and in particular in that causing undesirable fog. From this viewpoint, a method for obtaining a homogeneous solution to suppress the generation of the by-product is disclosed in JP-A-55-40607, in which fog still remains unsolved.

In JP-A-9-127643, disclosed is a method for producing silver salt based on simultaneous measuring and addition of an alkali metal salt solution and silver nitrate solution, and is specified as simultaneous addition of aqueous sodium behenate solution and isopropyl alcohol. While the method is successful in at least lowering the high pH during the reaction to the medium range and thereby in suppressing the generation amount of silver oxide, fog still cannot totally be cleared due to a weak reducibility of isopropyl alcohol.

As described above, preparation of fatty acid silver salt needs particular accounts such that eliminating as possible reducible substances during the formation of fatty acid silver salt, controlling the grain size and controlling the grain form, where all of them cannot be satisfied at a time by the conventional method.

In the production of a photothermographic material using the fatty acid silver salt, a photosensitive layer thereof is often formed by coating a coating liquid containing an organic solvent such as toluene, methyl ethyl ketone or methanol. Using an organic solvent as the solvent, however, is not only disadvantageous in terms of safety in the production processes, adverse effects on human body, and high cost ascribable to the solvent recovery or the like, but is also inappropriate in terms of providing an environment-conscious photothermographic material.

Thus a method for forming the photosensitive layer using a water-base coating liquid is proposed. For example, JP-A-49-52626 and JP-A-53-116144 disclose cases using gelatin as a binder. In JP-A-50-151138, a case using polyvinyl alcohol as a binder is described.

A case with a combined use of gelatin and polyvinyl alcohol is found in JP-A-60-61747. As another exemplary case, the photosensitive layer using a water-soluble polyvinyl acetal as a binder is described in JP-A-58-28737.

As is clear from the above, using a water-soluble binder allows the photosensitive layer to be formed with a water-base coating liquid and is beneficial from environmental and economic viewpoints. The water-soluble polymer binder is, however, less compatible with the fatty acid silver salts, which will fail in obtaining a coated film with a surface quality agreeable to the practical use, will result in brownish to yellowish tone of the silver image after the development afar from intrinsically preferable black tone, and will result in increased fog. Thus only afforded was a photothermographic material whose property being significantly degraded and commercially unsuccessful.

In order to obtain practically agreeable quality of the coated surface using the water-base coating liquid containing a fatty acid silver salt, the fatty acid silver salt must be kept in a finely dispersed state in the water-base solution without causing agglomeration. Discovery of a method for finely dispersing the fatty acid silver salt is thus desired. One method generally accepted relates to such that producing a hydrophobic grain dispersion of a fatty acid silver salt, separating the grain there from by filtration to obtain a solid matter, and re-dispersing the solid matter after being mixed with a dispersing agent as described by D. Kloosterboer in Imaging Processes and Materials, Neblette's 8th ed., edited by Sturge, V. Walworth and A. Shepp, p.279, (1989).

Fine dispersion operation of the fatty acid silver salt can be effected by mechanical dispersion in the presence of a dispersing agent using a known pulverizing means (e.g., high-speed mixer, homogenizer, high-speed impact mill, banbury mixer, homomixer, kneader, ball mill, vibration ball mill, epicyclic ball mill, attritor, sand mill, bead mill, colloid mill, jet mill, roller mill, trommel and high-speed stone mill). These methods, however, produce only a coating liquid including a lot of agglomerated grains and are thus causative of degraded surface quality, and, worse than all, tend to indiscriminately cleave the primary grains of the fatty acid silver salt which are originally crystallized as a water-insoluble salt, so that excessive silver nuclei are generated on the crystal cleavage plane of the grains and thereby to increase fog.

On the other hand, JP-B-7-119953 (the code "JP-B" as used herein means an "examined Japanese Patent Publication"), JP-A-8-137044 and JP-A-8-238848 disclose methods such that finely dispersing the fatty acid silver salt by pressure treatment. The methods, however, relate to an organic solvent-base dispersion and stand on a concept different from solving the foregoing problem.

In JP-A-9-127643, disclosed is a method such that obtaining a dispersion of the fatty acid silver salt by simultaneous measuring and addition of an alkali metal salt solution and silver nitrate solution, and then directly desalting the dispersion by dialysis or ultra-filtration. This method is preferable at least in that the primary grain obtained in the crystallization process of the fatty acid silver salt can be incorporated as intact into the photosensitive layer without being crushed. The method, however, still suffers from problems in agglomeration of the grains under a condition of high salt concentration, and in thickening during concentration of the dispersion, which makes the method difficult to be accepted as a measure for obtaining a practical coating liquid.

Another problem resides in that vigorous stirring is required when the alkali metal salt solution and silver nitrate solution are mixed in order to obtain a fine and monodisperse grains of the fatty acid silver salt. In particular, since a solution of a fatty acid alkali metal salt dissolved at a high temperature will instantaneously deposit crystal due to abrupt cooling upon the addition, a slow dilution speed and moderate fluidization will undesirably result in large and coarse grains. Raising the stirring speed during the addition into a tank in which a gas/liquid interphase is formed, however, causes entrainment of the air. Since the fatty acid silver salt grains are strongly hydrophobic and will adhere on the surface of the entrained air bubbles, which not only prevents bubble rupture but also causes agglomeration of adjacent grains on the surface of the bubbles. The liquid such entraining the air appears like a whipped cream, and for the case of desalting the by-produced salt through ultra-filtration, this will significantly degrade the handling property, and the agglomerated grains will clog the filtration membrane.

Temperature of the reaction liquid after the reaction between the silver ion-containing solution and the solution of a fatty acid alkali metal salt is preferably kept around the room temperature, since too high temperature will result in growth of the grains by a physical ripening process. Whereas, the temperature needs be kept at 50° C. or above to obtain a stable solution of an alkali metal salt of a long-chained fatty acid, so that it is necessary to ensure a rapid heat exchange so as to cancel the heat introduced with the added liquid. In this point, a measure for providing a jacket vessel to a tank or the like suffers from a problem in that a heat-exchangeable area reduces as volume of the reaction liquid increases.

As described above, a stable method for preparing a water-base coating liquid containing fatty acid silver salt grains capable of affording an excellent coated surface quality and optical properties such as low haze and low fog has not been discovered yet.

It is therefore an object of the present invention to provide a method for preparing fatty acid silver salt grains exhibiting an excellent dispersion stability and coating property when made into a dispersion, and can provide, when incorporated into a photothermographic material, an excellent fog preventive property during storage, and an excellent image stability and light transmissivity after the heat-development process.

SUMMARY OF THE INVENTION

The present inventors found after extensive investigations for achieving the above object that excellent non-photosensitive fatty acid silver salt grains can be obtained by mixing and reacting a silver ion-containing aqueous solution with a solution of a fatty acid alkali metal salt within a closed mixing means.

The "closed mixing means" as described herein refers to a means such that the inner space of which being filled with the liquids to be mixed, and having substantially no air phase, or in other words, having no gas/liquid interphase.

That is, the present invention is to provide a method for preparing non-photosensitive fatty acid silver salt grains having the step of reacting a silver ion-containing solution, the solvent of which being water, or a mixture of water and an organic solvent, with a solution of a fatty acid alkali metal salt, solvent of which being water, an organic solvent, or a mixture of water and an organic solvent, to obtain a fatty acid silver grain; in which the reaction is proceeded by mixing the silver ion-containing solution and the solution of the alkali metal salt of the fatty acid within a closed mixing means.

In the method for preparing non-photosensitive fatty acid silver salt grains of the present invention, it is preferable to further charge water, or a mixture of water and an organic solvent into the closed mixing means. It is particularly preferable that the water or the mixture contains a dispersing agent. It is also preferable to circularly feed back at least a part of a reacted mixture obtained after the reaction to the closed mixing means. It is still also preferable to cool the reacted mixture obtained after the reaction.

The present invention is to provide also an apparatus for preparing a non-photosensitive fatty acid silver salt grains having; a first feed means for feeding a silver ion-containing solution, the solvent of which being water or a mixture of water and an organic solvent, to a closed mixing means described later; a second feed means for feeding a solution of a fatty acid alkali metal salt, solvent of which being water, an organic solvent, or a mixture of water and an organic solvent, to the closed mixing means; a third feed means for feeding water, or a mixture of water and an organic solvent to the closed mixing means; and the closed mixing means for mixing matters fed from the first feed means, the second feed means and the third feed means, and discharging a liquid containing non-photosensitive fatty acid silver salt grains. It is preferable that the apparatus additionally has a cooling means for cooling the liquid containing non-photosensitive fatty acid silver salt grains discharged from the closed mixing means.

The present invention is to provide still also an apparatus for preparing non-photosensitive fatty acid silver salt grains having; a first feed means for feeding a silver ion-containing solution, the solvent of which being water or a mixture of water and an organic solvent, to a closed mixing means described later; a second feed means for feeding a solution of a fatty acid alkali metal salt, solvent of which being water, an organic solvent, or a mixture of water and an organic solvent, to the closed mixing means; the closed mixing means for mixing matters fed from the first feed means, the second feed means and a third feed means described next, and discharging a liquid containing non-photosensitive fatty acid silver salt grains; and the third feed means for feeding back at least a part of the liquid containing non-photosensitive fatty acid silver salt grains discharged from the closed mixing means to said closed mixing means. The apparatus preferably has a cooling means for cooling the liquid containing non-photosensitive fatty acid silver salt grains discharged from the closed mixing means. In such apparatus, the closed mixing means is preferably a mixing apparatus having rotating blades in a closed vessel. A linear velocity at the outermost periphery portion of such rotating blades is preferably 1 to 50 m/second, and a stirring power of such mixing apparatus is preferably 0.1 to 10 kW per liter of a reaction mixture.

The above and other objects and features of the invention are apparent to those skilled in the art from the following referred embodiments thereof when considered in conjunction with the accompanied wings.

DETAILED DESCRIPTION OF THE INVENTION

The method for preparing the non-photosensitive fatty acid silver salt grains of the present invention will be detailed hereinafter.

The method for preparing the non-photosensitive fatty acid silver salt grains of the present invention is such that having the step of reacting a silver ion-containing solution, the solvent of which being water or a mixture of water and an organic solvent, with a solution of a fatty acid alkali metal salt, solvent of which being water, an organic solvent, or a mixture of water and an organic solvent, to obtain fatty acid silver salt grains; and in which the reaction is proceeded by mixing the silver ion-containing solution and the solution of the alkali metal salt of the fatty acid within a closed mixing means. It is also allowable to provide a plurality of such closed mixing means in parallel in the present invention.

Figure 1:
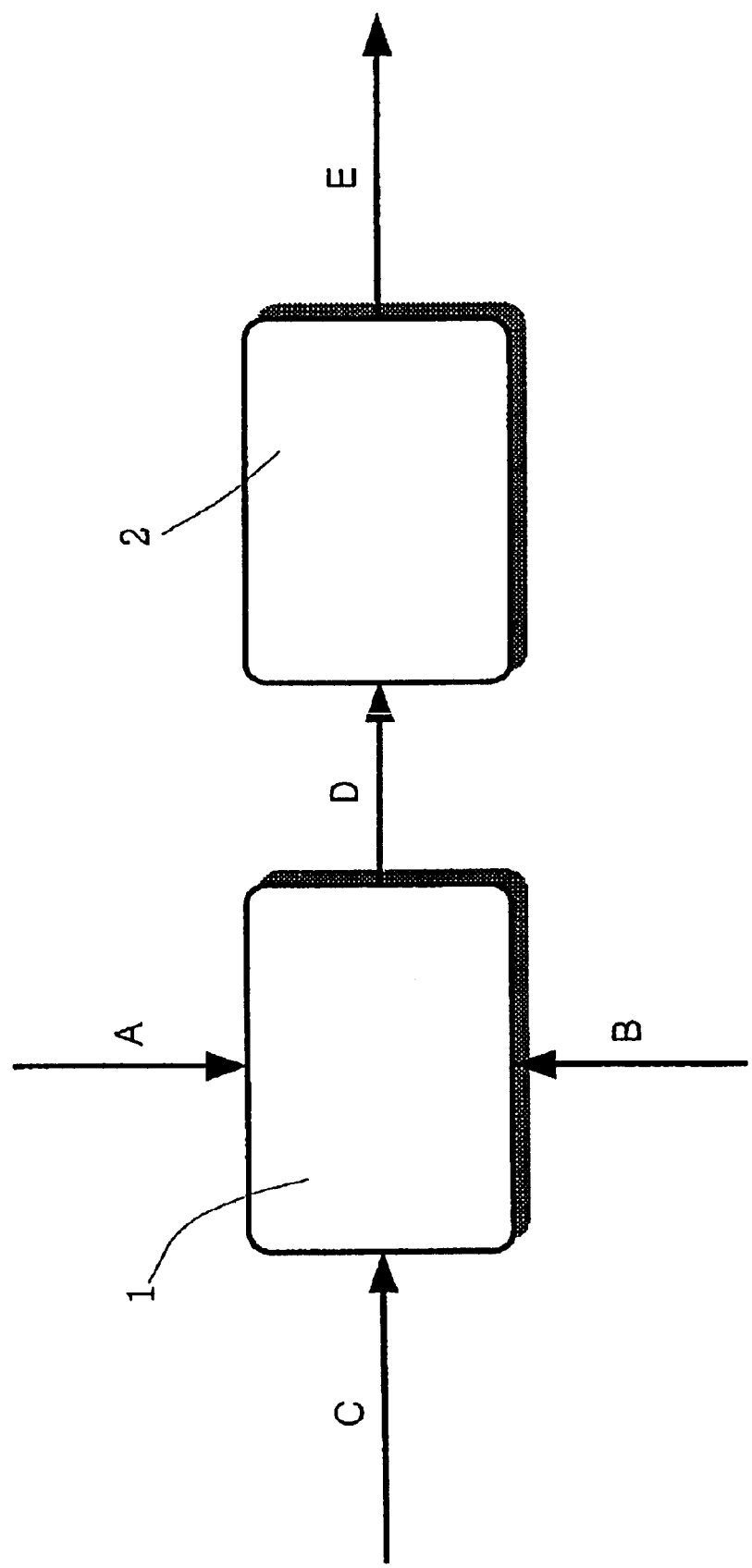
FIG. 1 is a schematic diagram showing a method for preparing the non-photosensitive fatty acid silver salt grains of the present invention.

FIG. 1 shows a schematic diagram showing a method for preparing the non-photosensitive fatty acid silver salt grains of the present invention. Symbol 1 is used for a mixing apparatus which is closed and filled with the liquids, and 2 for a heat exchanger. In this figure, "A" is a symbol for a silver ion-containing solution, "B" for a solution of a fatty acid alkali metal salt, and "C" for water or a mixture of water and an organic solvent, or a reaction mixture containing the non-photosensitive fatty acid silver salt grains obtained after the reaction. These liquids are joined within the mixing apparatus to prepare the reaction mixture "D" containing fatty acid silver salt grains, which is then fed to a heat exchanger 2 to be cooled.

Figure 2:
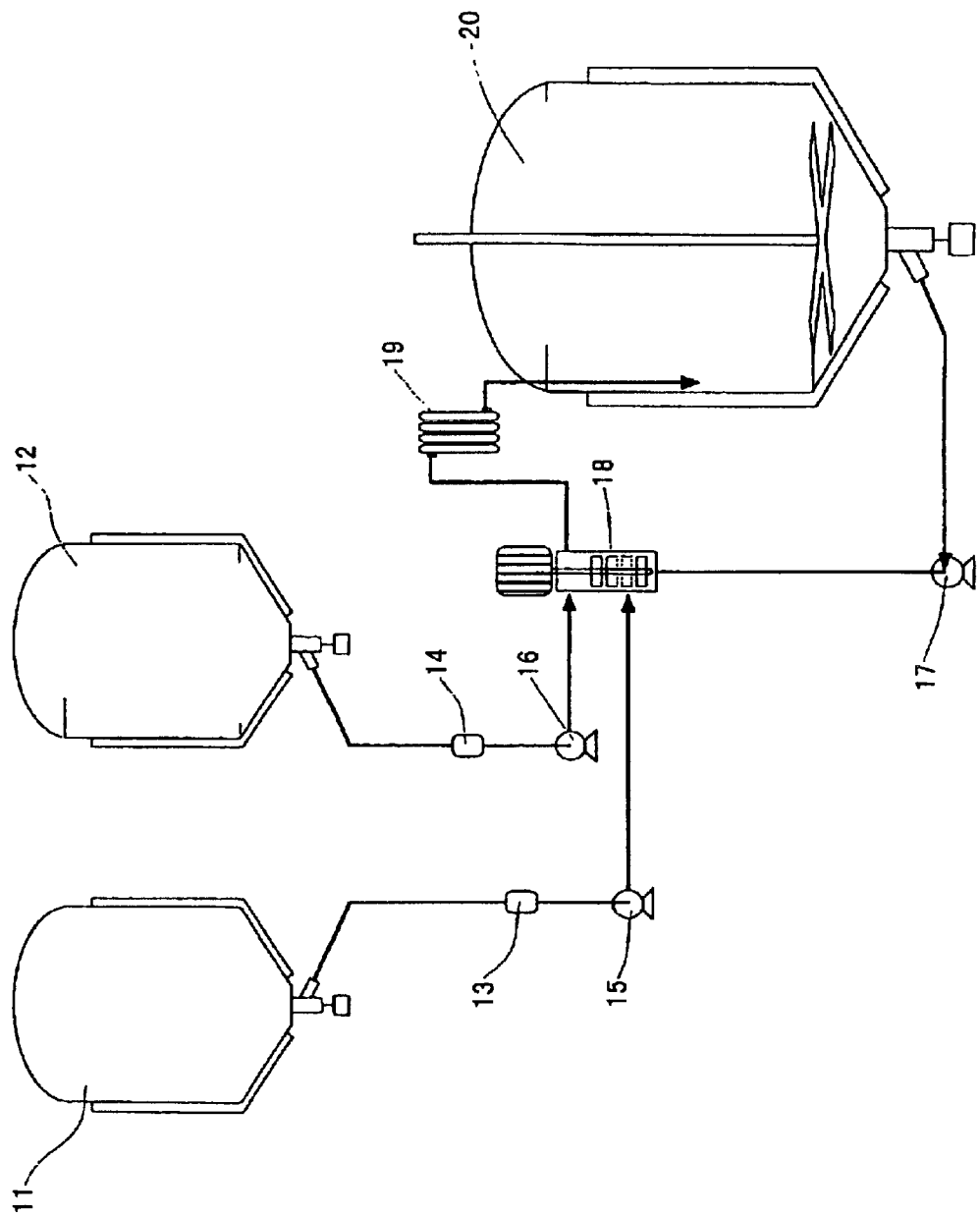
FIG. 2 is a schematic diagram showing an exemplary constitution of an apparatus used for preparing the non-photosensitive fatty acid silver salt grains of the present invention.

FIG. 2 shows one embodiment relating the method for preparing the non-photosensitive fatty acid silver salt grains. Symbols 11 and 12 in the figure represent tanks for storing under predetermined temperatures the silver ion-containing solution and the solution of the fatty acid alkali metal salt, respectively. Symbols 13 and 14 represent flow meters for measuring flow rates of these liquids fed via pumps 15 and 16 to a liquid-filled closed mixing apparatus 18. In this embodiment, provided as a third component is a pump 17 for feeding the obtained dispersion of the fatty acid silver salt grains back to the liquid-filled mixing apparatus 18. The liquid after completion of the reaction within the mixing apparatus 18 is introduced into a heat exchanger 19, and is rapidly cooled and introduced into tank 20 for the obtained mixture.

Figure 3:
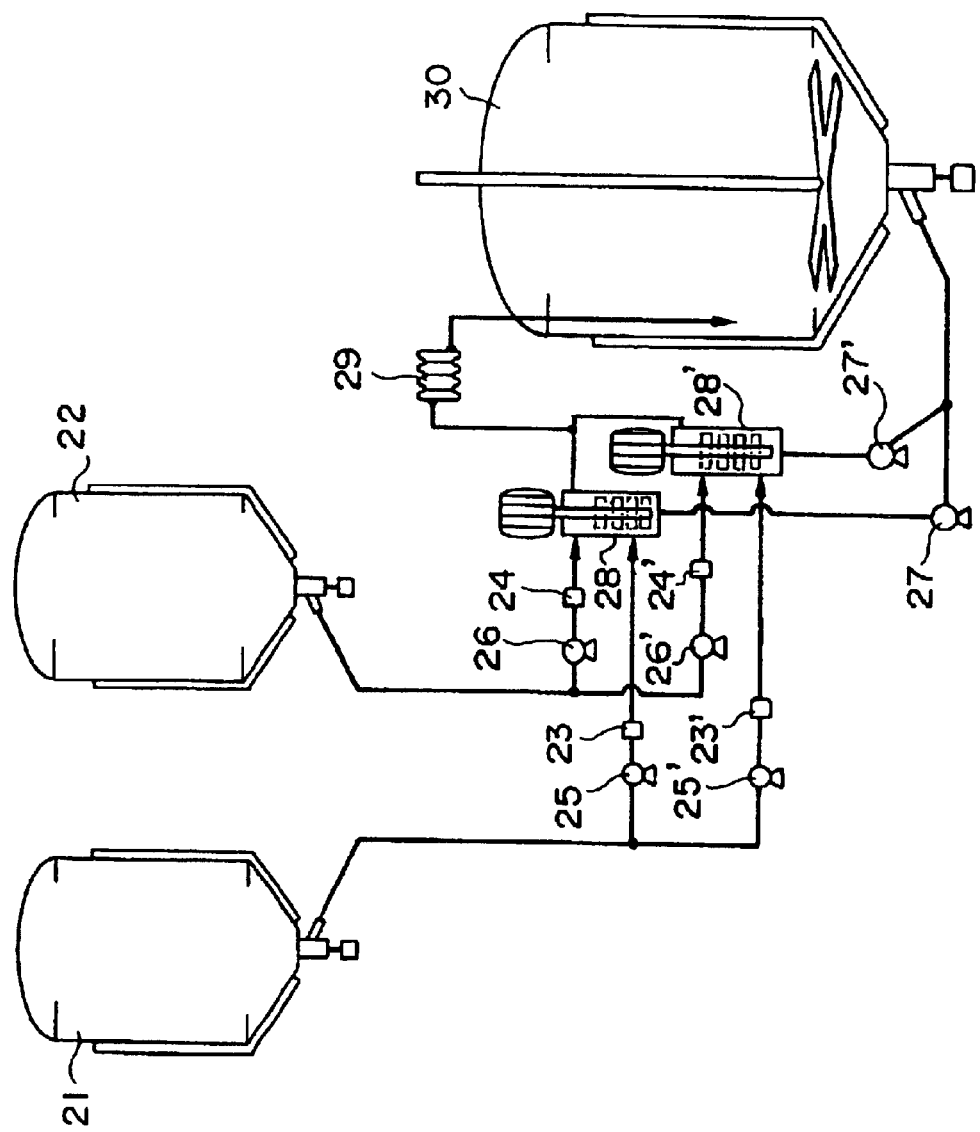
FIG. 3 is a schematic diagram showing another exemplary constitution of an apparatus used for preparing the non-photosensitive fatty acid silver salt grains of the present invention.

FIG. 3 shows another embodiment relating the method for preparing the non-photosensitive fatty acid silver salt grains of the present invention. Symbols 21 and 22 in the figure represent tanks for storing under predetermined temperatures the silver ion-containing solution and the solution of the fatty acid alkali metal salt, respectively. Symbols 23, 23', 24 and 24' represent flow meters for measuring flow rates of these liquids fed via pumps 25, 25', 26 and 26' to liquid-filled closed mixing apparatus 28 and 28. In this embodiment, provided as third components are pumps 27 and 27' for feeding the obtained dispersions of the fatty acid silver salt grains back to the mixing apparatus 28 and 28'. The liquids after completion of the reaction within the mixing apparatus 28 and 28' are introduced into a heat exchanger 29, and are rapidly cooled and introduced into tank 30 for the obtained mixtures. Thus, the method for preparing the non-photosensitive fatty acid silver salt grains of the present invention may use a single closed mixing apparatus or two or more closed mixing apparatus in parallel. In the latter, the solutions can be supplied to each closed mixing apparatus in equal amount.

Figure 4:
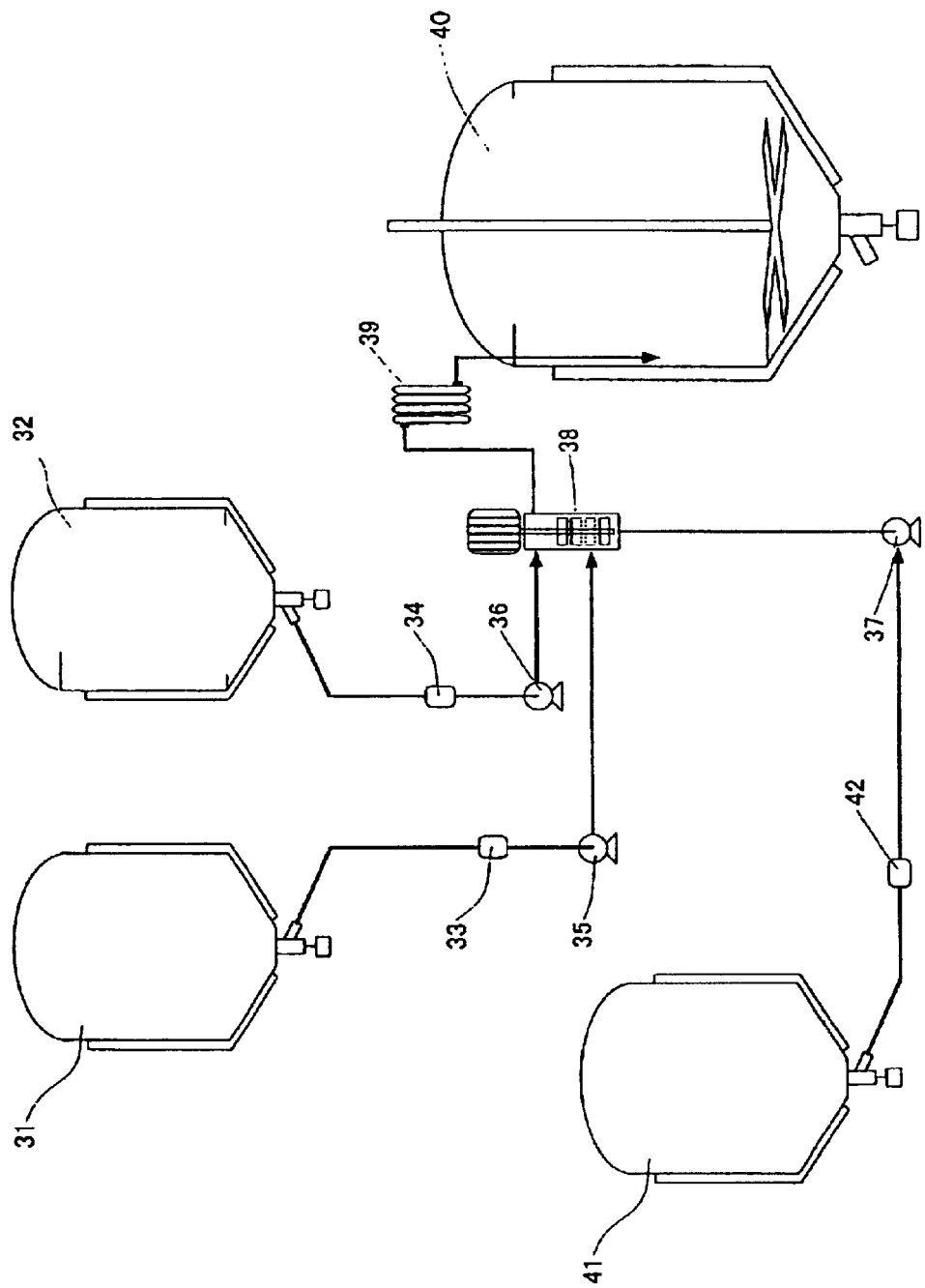
FIG. 4 is a schematic diagram showing still another exemplary constitution of an apparatus used for preparing the non-photosensitive fatty acid silver salt grains of the present invention.

FIG. 4 shows one embodiment relating the method for preparing the non-photosensitive fatty acid silver salt grains according to the present invention. Symbols 31 and 32 in the figure represent tanks for storing under predetermined temperatures the silver ion-containing solution and the solution of the fatty acid alkali metal salt, respectively. Symbols 41 in the figure represent tanks for storing under predetermined temperatures water, or a mixture of water and an organic solvent, which may contain a dispersing agent. Symbols 33, 34 and 42 represent flow meters for measuring flow rates of these liquids fed via pumps 35, 36 and 37 to a liquid-filled closed mixing apparatus 38. The liquid after completion of the reaction within the mixing apparatus 38 is introduced into a heat exchanger 39, and is rapidly cooled and introduced into tank 40 for the obtained mixture.

The silver ion-containing solution and the solution of the fatty acid alkali metal salt can be prepared and stored under predetermined temperature in the tank for storing. Alternatively, the solutions can be introduced into the tank after preparation and stored under predetermined temperature.

There is no specific limitation on types of the heat exchanger, and beneficial examples thereof include a shell-and-tube heat exchanger, heat pipe exchanger, double-pipe exchanger, coil-in-box cooler, cascade cooler and spiral plate exchanger.

A flow meter for measuring the silver ion-containing solution is preferably an electromagnetic flow meter or mass flow meter having a measurement error of 1% or below and a time constant of less than one second.

Preferable pumps include those capable of feed-back control based on the obtained measurement values from the above flow meter (for example, rotary pump, sanitary pump, gear pump, Mono pump, plunger pump and diaphragm pump), or those capable of affording a stable discharge with a quantitative error below 1% (for example, gear pump, Mono pump, plunger pump and diaphragm pump). Those with a pulsation factor of less than 5% are preferable.

The silver ion-containing solution used in the present invention preferably has a pH value of 1 to 6, and more preferably 1.5 to 4. An arbitrary acid or base can be added for further pH adjustment.

Silver ion concentration of the silver ion-containing solution used in the present invention may arbitrarily be selected, where a preferable range as expressed in molar concentration is from 0.03 to 6.5 mol/L, and more preferably 0.1 to 5 mol/L.

To successfully form the fatty acid silver salt grains in the present invention, at least one of the silver ion-containing solution, the alkali metal salt solution of the fatty acid and a solution preliminarily provided in the reaction field must contain an organic solvent in an amount so that the alkali metal salt of the fatty acid can fully be dissolved to give a substantially transparent solution, rather than forming string-like aggregates or micells. While single use of an organic solvent is also allowable, use of a mixed solution with water is more preferable.

The organic solvent used in the present invention may be of any type so far as having water solubility and above-described properties, whereas those adversely affecting photographic properties are not preferable. Preferable examples of such solvent include water-miscible alcohol and acetone, and more preferable examples relate to tertiary alcohol having a carbon number of 4 to 6. The fatty acid composing the alkali metal salt of the fatty acid is such that being capable of generating a silver salt which is relatively stable against the light, but can produce silver image when heated at 80° C. or higher in the presence of light-exposed photocatalyst (e.g., latent image of photosensitive silver halide) and a reducing agent. The fatty acid is preferably a long-chained fatty carboxylic acid specifically having a carbon number of 10 to 30, more preferably 12 to 26. Preferable examples of the fatty carboxylic acid include cerotic acid, lignoceric acid, behenic acid, erucic acid, arachidinic acid, stearic acid, oleic acid, lauric acid, caproic acid, myristic acid, palmitic acid, maleic acid, fumaric acid, tartaric acid, linolic acid, butyric acid, camphoric acid and mixtures thereof.

The alkali metal composing the alkali metal salt of the fatty acid used in the present invention is typified as sodium or potassium. The alkali metal salt of the fatty acid can be obtained by adding NaOH or KOH to the fatty acid, in which it is preferable to limit an amount of use of the alkali metal less than that of the fatty acid so that a part of the fatty acid will remain unreacted. The amount of the remaining fatty acid is 3 to 50 mol % relative to the total fatty acid, and preferably 3 to 30 mol %. It is also allowable in the preparation to add an excessive amount of an alkali and then add acid such as nitric acid or sulfuric acid to neutralize the excessive portion of the alkali.

The silver-ion containing solution, the solution containing the fatty acid alkali metal salt; or the solution pre-charged in the closed mixing apparatus to which two above solutions will be charged may be added with a dispersing agent such as, for example, a compound expressed by the general formula (1) of JP-A-62-65035, a water-soluble N-heterocyclic compound having a solubility-expressing group as disclosed in JP-A-62-150240, an inorganic peroxide as disclosed in JP-A-50-101019, a sulfur compound as disclosed in JP-A-51-78319, a disulfide compound as disclosed in JP-A-57-643 and hydrogen peroxide.

The solution of the fatty acid alkali metal salt preferably contains the organic solvent in an amount of 3 to 70 vol % of water volume, and preferably 5 to 50 vol %. Since an optimum solvent volume can vary depending on the reaction temperature, it is preferable to determine the optimum volume in a trial-and-error manner.

Concentration of the fatty acid alkali metal salt used in the present invention is preferably 5 to 50 wt %, more preferably 7 to 45 wt %, and still more preferably 10 to 40 wt %.

A desired fatty acid silver salt can be prepared by simultaneously adding the silver ion-containing solution and the solution of fatty acid alkali metal salt to the closed mixing means. In such a case, it is preferable that 10 to 100%, more preferably 30 to 100%, and still more preferably 50 to 100% of the total amount of addition of silver is added simultaneously with the solution containing a nearly equal molarity of the fatty acid alkali metal salt. When either solution is precedently added, the silver ion-containing solution in precedence is more preferable.

Temperature of the silver-ion containing solution or the solution of the fatty acid alkali metal salt may appropriately be selected in order to obtain desired grains. The temperature of the silver-ion containing solution is preferably selected to 5 to 60° C., and more preferably 5 to 40° C., for the purpose of ensuring stability of the liquid. The temperature of the solution of the fatty acid alkali metal salt is preferably 50 to 90° C., and more preferably 60 to 85° C., for the purpose of keeping a certain temperature required for avoiding crystallization or solidification of the alkali soap. Tanks for storing these solutions are preferably equipped with means for maintaining such a temperature.

Various approaches are allowable for preparing the fatty acid silver salt grains by the present invention. To obtain the grains appropriate for the present invention, it is preferable to lower solubility of the fatty acid silver salt in the reaction field. The present inventors have found from the investigations that the longer the duration of the reaction became, the smaller the grain size became. It was thus concluded that, to obtain a desired grain size, the reaction period must be determined by a trial-and-error manner.

There is no particular limitation on the apparatus used for producing the silver salt. As for the closed mixing apparatus used in the present invention, in particular, a variety of available models include those of bulk stirring type using anchor wing or paddle wing; emulsifying dispersion type such as dissolver and homogenizer; static mixing apparatus such as static mixer and sluzer mixer; and those based on combination of two these types. The solvent preliminarily charged in the reaction vessel is typically water, where also available is a mixed solution of water and an organic solvent same as that used in the silver ion-containing solution or the solution of fatty acid alkali metal salt.

In the liquid mixing process, too small stirring force will result in insufficient mixing, whereas too large stirring force will cause heating or cavitation, so that the stirring force will have a preferable range. For the case of using a mixing apparatus having rotating blades, it is preferable to select a linear velocity at the outermost periphery portion of such rotating blades within a range from 1 to 50 m/second, and more preferably from 1 to 30 m/second, and a stirring power consumption per unit liquid volume within a range from 0.1 to 10 kW/L, and more preferably from 0.5 to 5 kW/L. It is also acceptable to employ, as cavitation suppressing means, a method for reducing dissolved air in the liquid, or raising pressure within the mixing apparatus by approx. 0.1 to 2 kgf/cm$^2$ as compared with the atmospheric pressure.

While there is no particular limitation on materials composing the closed mixing apparatus provided that they exhibit an appropriate mechanical strength, preferable is a material such that being inert to the silver ion-containing solution, the solution of the fatty acid alkali metal salt, and an organic solvent employed. Since temperature of the solution of the fatty acid alkali metal salt is 50° C. or above in general, it is also important to select a thermally stable material. Typical materials meeting these requirements include stainless steels (e.g., SUS304 and SUS316); titanium or titanium alloys; metal materials covered, for example, with glass lining, ceramic or fluorocarbon resin; composite resins reinforced with glass fiber or Kevlar; and engineering plastics such as polyacetal and modified polyphenylene oxide.

Order of the addition of the silver ion-containing solution (liquid "A") and the solution of a fatty acid alkali metal salt (liquid "B") may be any one of such that adding both liquids "A" and "B" in the same closed mixing apparatus; such that adding either one of which in the upper stream side of the closed mixing apparatus and adding the other in the closed mixing apparatus; and such that adding both liquids "A" and "B" in the upper stream side of the closed mixing apparatus. In addition to the above liquids "A" and "B", it is also allowable to add a third liquid in the same closed mixing apparatus; where the third liquid being water, a mixture of water and an organic solvent used in the silver ion-containing solution and the solution of a fatty acid alkali metal salt, or a reaction liquid in which the non-photosensitive fatty acid silver salt grains are already produced. It is further allowable to add any two liquids from the liquids "A", "B" and "C" in the upper stream side of the closed mixing apparatus in an arbitrary order and to add the remaining liquid in the closed mixing apparatus; or to add three all liquids in the upper stream side of the closed mixing apparatus. The closed mixing apparatus can be composed of a plurality of units connected in series, and the individual unit can contain one or two liquids (for example, a first unit contains the liquid "A" and a second unit in the next stage contains the liquid "B"; or both of the first and second units contain both liquids "A" and "B"; or the first unit contains the liquid "A" and the second unit contains the liquids "A" and "B").

Also duration of the addition of the silver ion-containing solution and the solution of the fatty acid alkali metal salt is arbitrarily selected, and the addition can be effected at a constant rate, or in a accelerated or decelerated mode according to an arbitrary time function.

Possible methods for rapidly cooling temperature of the liquid obtained after the reaction between the silver ion-containing solution and the solution of the fatty acid alkali metal salt include such that previously cooling liquids to be fed to the mixing apparatus, such liquids being any one of the silver ion-containing solution, water, a mixture of water and an organic solvent, or the reaction liquid containing the fatty acid silver salt grains; such that cooling the mixing apparatus per se; and such that providing a heat exchanger between the mixing apparatus and the tanks. The liquid temperature obtained after the reaction between the silver ion-containing solution and the solution of fatty acid alkali metal salt is preferably 5 to 70° C., more preferably 10 to 50° C., and still more preferably 20 to 45° C. The cooling rate is preferably such that ensuring a desired temperature within 0.05 to 10 seconds, more preferably 0.05 to 5 seconds, and still more preferably 0.05 to 1 seconds after both liquids are joined.

Fatty acid alkali metal salt particles thus prepared is introduced into the tank for storing the obtained mixture. The mixture is preferably mixed with stirring to homogenate the mixture in the tank. As for the mixing means in the tank, a variety of available models include those of bulk stirring type using anchor wing or paddle wing; emulsifying dispersion type such as dissolver and homogenizer; static mixing apparatus such as static mixer and sluzer mixer; and those based on combination of two these types.

Sphere-equivalent diameter of the fatty acid silver salt grains prepared in the present invention is preferably 0.1 to 0.8 $\mu$m, and more preferably 0.1 to 0.6 $\mu$m. Long edge/short edge ratio of the grain is preferably 1 to 4, more preferably 1 to 3, and still more preferably 1 to 2. Aspect ratio of the grain [grain size (circle-equivalent diameter) of the major plane/grain thickness] is preferably 2 to 30, and more preferably 2 to 15. Grain thickness is preferably 0.01 to 0.20 $\mu$m, and more preferably 0.01 to 0.15 $\mu$m. The grains satisfying the above requirements preferably account for 30 to 100% of the projected area of the total grains, more preferably 50 to 100%, and still more preferably 70 to 100%.

Particle size distribution of the organic silver salt is preferably of monodisperse as possible. Coefficient of variation of the grain size of the fatty acid silver salt grain is preferably 20% or below, more preferably 18% or below, and still more preferably 15% or below, where the coefficient of variation is defined as a value obtained by dividing a standard deviation of a grain diameter by the grain diameter and then multiplied by 100. An exemplary procedure for the measurement include irradiating laser light to the fatty acid silver salt dispersed in a solution; deriving an autocorrelation function with respect to the time-dependent fluctuation in the scattered light intensity; and thereby obtaining grain size (volume weighted mean diameter), which is known as the dynamic light scattering method.

A water-soluble dispersing agent can be added to the silver ion-containing solution, the solution of the fatty acid alkali metal salt or the reaction liquid in the present invention. The dispersing agent can be contained in the reaction liquid in the process of producing the fatty acid silver salt grains; in a separately prepared solution; or in the finished liquid after the fatty acid silver salt grains are produced. The dispersing agent can be of any type so far as it can disperse the generated fatty acid silver salt grains, and specific examples thereof can be referred to those used for the fatty acid silver salt described later.

The fatty acid silver salt grains available in the present invention will have a form of solid microgram dispersion assisted by the dispersing agent so as to achieve a small grain size and an agglomeration-free nature. In the process of producing such solid microgram dispersion, it is preferable to avoid only the agglomeration while preventing the produced grains from being fractured. Such status can be judged by comparing TEM (transmission electron microscope) photographs of the grains taken before water washing and after the dispersion. The grains produced according to the method of the present invention are preferably such that the projected area of which being not altered by 30% or more, more preferably 20% or more, and still more preferably 10% or more, when the average grain sizes before the water washing and after the dispersion are compared. The dispersion is preferably effected by converting a water-base dispersion of the fatty acid silver salt into a high-pressure and high-speed flow, which is followed by an abrupt pressure drop.

It is preferable that the dispersion contains substantially no photosensitive silver salt during the dispersion, since presence of the photosensitive silver salt during the dispersion may increase fog and significantly lower the sensitivity. In the present invention, a content of the photosensitive silver salt in the water-base dispersion to be dispersed is 0.1 mol % or less relative to 1 mol of the organic acid silver salt contained therein, without any intentional addition of the photosensitive silver salt.

Dispersion apparatus and technologies available for implementing the above dispersion in the present invention are detailed, for example, in "Bunsankei Reoroji to Bunsanka Gijutsu (Dispersed System Rheology and Dispersion Technology)", by Toshio Kajiuchi and Hiroki Usui, 1991, issued by Sinzansha Shuppan, p.357–403; "Kagaku Kogaku no Sinpo (Advances in Chemical Engineering) Vol.24", ed. Tokai Section, The Society of Chemical Engineers, 1990, issued by Maki Shoten, p.184–185. A dispersion method employed in the present invention is such that feeding the water-base dispersion containing at least fatty acid silver salt into a piping while being pressurized with a high-pressure pump or the like, allowing the dispersion to pass through a narrow slit, and then causing an abrupt pressure drop to the dispersion thereby completing a fine dispersion.

As for a high-pressure homogenizer available in the present invention, an uniform and effective dispersion is generally considered to be-effected by dispersion forces such as (a) "shearing force" generated when dispersoid passes through a narrow gap under a high pressure and at a high speed, and (b) "cavitation force" generated when the dispersoid is released from the high pressure state to the normal pressure state. Galling homogenizer has long been known as such kind of dispersion apparatus, in which a pressure-fed solution to be dispersed is converted into a high-speed flow at a narrow gap on a cylinder surface, then rushed to be collided with the peripheral wall, thereby allowing emulsification or dispersion assisted by the impact force. Operating pressure is, in general, selected in a range from 100 to 600 kg/cm$^2$, and flow rate in a range several to 30 m/second. There is also proposed an apparatus such that having a saw-toothed high flow rate portion to increase the number of collision for a higher dispersion efficiency. Recent new developments for enabling the dispersion at a still higher pressure range typically include Microfluidizer (product of Microfluidex International Corporation), and Nanomizer (product of Tokushu Kika Kogyo Co., Ltd.).

In the present invention, it is possible to disperse the organic silver salt so as to attain a desired grain size by properly adjusting the flow rate, pressure difference at the time of the pressure drop and the number of repetition of the process. Taking photographic properties and the grain size into account, the flow rate is preferably from 200 to 600 m/sec, more preferably from 300 to 600 m/sec, and the pressure difference at the pressure drop is preferably from 900 to 3000 kg/cm$^2$, and more preferably from 1500 to 3000 kg/cm$^2$. The number of repetition of the process is selectable as required. While this is generally selected as once to as much as 10 times, once to as much as 3 times is preferred from the viewpoint of productivity. Raising the temperature of such water-base dispersion under high pressure is undesirable from the viewpoint of dispersibility and photographic properties, that is, raising the temperature above 90° C. tends to result in increased grain size and increased fogging. It is thus preferable in the present invention to provide a cooling step before the conversion into the high-pressure, high-speed flow and/or after the pressure drop, to maintain the temperature of the water-base dispersion within a range from 5 to 90° C., more preferably from 5 to 80° C., and still more preferably 5 to 65° C. Providing such cooling step is particularly effective when the dispersion is proceeded under the pressure as high as 1500 to 3000 kg/cm$^2$. A cooler is properly selected, depending on the required capacity of heat exchange, from those being equipped with a double pipe or triple pipe as combined with a static mixer; shell-and-tube heat exchanger; and coiled heat exchanger. The diameter, wall thickness and material of the pipe are properly be selected, considering the operating pressure, so as to improve the efficiency of the heat exchange. Coolants available for the cooler is selectable, depending on the required amount of heat exchange, from well water at 20° C.; cold water at 5 to 10° C. fed from a chiller; and, as requested, ethylene glycol/water at −30° C.

The dispersing agent can be properly selected from, for example, synthetic anionic polymers such as polyacrylic acid, copolymers of acrylic acid, maleic acid copolymers, maleic acid monoester copolymers and acryloylmethylpropanesulfonic acid copolymers; semisynthetic anionic polymers such as carboxymethylated starch and carboxymethylcellulose; anionic polymers such as alginic acid and pectic acid; anionic surfactants such as disclosed in JP-A-52-92716 and WO88/04794; compounds disclosed in JP-A-9-179243; known anionic, nonionic and cationic surfactants; other known polymers such as polyvinyl alcohol, polyvinylpyrrolidone, carboxymethyl cellulose, hydroxypropyl cellulose, and hydroxypropylmethyl cellulose; naturally occurring polymers such as gelatin and the like.

A concentration of the dispersing agent is preferably 1 to 30 wt % of the fatty acid silver salt, and more preferably 3 to 20 wt %.

The produced dispersion can be stored under stirring in order to prevent precipitation of the micrograms during storage, or stored in a highly viscous state by producing hydrophilic colloid (e.g., jelly state formed with gelatin). Further, it may be added with a preservative in order to prevent germ proliferation during the storage.

The fatty acid silver salt dispersion obtained by the present invention comprises at least a fatty acid silver salt and water. While there is no specific limitation on the ratio of the fatty acid silver salt and water, it is important to select the ratio so as to ensure an efficient film formation, considering Theological characteristics required for the stable coating, and the production speed depending on the dry moisture content. The fatty acid silver salt preferably accounts for 10 to 50 wt % of the total dispersion, and more preferably 10 to 30 wt %.

It is preferable to add a metal ion selected from the group consisting of Ca, Mg, Ce, Al, Zn and Ba in a form of a water-soluble salt other than halide. More specifically, the addition in a form of a nitrate or sulfate is preferable.

The metal ion selected from the group consisting of Ca, Mg, Ce, Al, Zn and Ba can be added at any time provided that it is immediately before the coating. That is, it may be added to the solution used for preparing the fatty acid silver salt or may preliminarily added in the reaction liquid; may be added during or immediately after the production of the fatty acid silver salt; or may be added before or after the preparation of the coating liquid. An amount addition of the metal is preferably $10^{-3}$ to $10^{-1}$ mol per mol of the fatty acid silver salt, and more preferably $5 \times 10^{-3}$ to $5 \times 10^{-2}$ mol.

While there is no particular limitation on an apparatus for implementing the preparation method of the present invention, a preferable apparatus relates to such that having a first feed means for feeding a silver ion-containing solution, the solvent of which being water or a mixture of water and an organic solvent, to a closed mixing means described later; a second feed means for feeding a solution of a fatty acid alkali metal salt, solvent of which being water, an organic solvent, or a mixture of water and an organic solvent, to the closed mixing means; a third feed means for feeding water, or a mixture of water and an organic solvent to the closed mixing means; and the closed mixing means for mixing matters fed from the first feed means, the second feed means and the third feed means, and discharging a liquid containing non-photosensitive fatty acid silver salt grains. It is preferable that the apparatus is additionally provided with a cooling means for cooling the liquid containing non-photosensitive fatty acid silver salt grains discharged from the closed mixing means (FIG. 4).

Another preferable apparatus for implementing the preparation method of the present invention relates to such that having a first feed means for feeding a silver ion-containing solution, the solvent of which being water or a mixture of water and an organic solvent, to a closed mixing means described later; a second feed means for feeding a solution of a fatty acid alkali metal salt, solvent of which being water, an organic solvent, or a mixture of water and an organic solvent, to the closed mixing means; the closed mixing means for mixing matters fed from the first feed means, the second feed means and a third feed means described next, and discharging a liquid containing non-photosensitive fatty acid silver salt grains; and the third feed means for feeding at least a part of the liquid containing non-photosensitive fatty acid silver salt grains discharged from the closed mixing means back to said closed mixing means. It is preferable that the apparatus is additionally provided with a cooling means for cooling the liquid containing non-photosensitive fatty acid silver salt grains discharged from the closed mixing means (FIG. 2).

In the apparatus shown in FIG. 2, a dispersion of the non-photosensitive fatty acid silver salt grains having a desired concentration can be prepared in the tank 20 by properly regulating the volume of the solution containing non-photosensitive fatty acid silver salt grains fed from the third feed means to the closed mixing apparatus. The concentration of the dispersion of the non-photosensitive fatty acid silver salt grains in the tank 20 becomes higher as the number of repetition of the circulation with the aid of the third feed means increases, so that a proper selection of the circulation conditions can afford a dispersion having a desired concentration. The concentration can be regulated, not only by adjusting such circulation conditions, but also by adjusting conditions for withdrawing the prepared dispersion. Thus a desired dispersion can efficiently be obtained by properly selecting the above conditions while sustaining the continuous operation. The tank (symbol 20 in FIG. 2, and symbol 40 in FIG. 4) accepting the produced dispersion of the fatty acid silver salt grains may further be provided with a mixing means such as a stirrer for homogenizing the content, a heat exchange means such as a jacket vessel, a liquid temperature measuring means, a level sensor for controlling the liquid volume, and an optional means for measuring physical properties such as pH, electric conductivity and viscosity.

The thermally processed image forming material composable with the non-photosensitive fatty acid silver salt prepared according to the method of the present invention will further be detailed.

The thermally processed image forming material preferably contains, as dispersed within a binder matrix, the above fatty acid silver salt as a reducible silver salt, and a reducing agent for reducing silver ions. A catalytic amount of a photocatalyst (preferably a photosensitive silver halide) is optionally used to provide photosensitivity. A toning agent for controlling color tone of silver image may be used as requested.

While the fatty acid silver salt can be used in a desired amount, a preferable range thereof is from 0.1 to 5 g/m$^2$, and more preferably 1 to 3 g/m$^2$.

The reducing agent is an arbitrary substance capable of reducing silver ion into metal silver, and is preferably an organic substance. Specific examples of the reducing agent are disclosed in the paragraphs [0043] to [0045] of JP-A-11-65021, and line 34 on page 7 to line 12 on page 18 of European Laid-Open Patent Publication No. 0803764A1.

An amount of addition of the reducing agent in the present invention is preferably 0.01 to 5.0 g/m$^2$, and more preferably 0.1 to 3.0 g/m$^2$, and in other words, it is preferably contained elsewhere on the image producing layer side in an amount of 5 to 50 mol % per mole of silver, and more preferably 10 to 40 mol %. The reducing agent is preferably contained in the image recording layer.

There is no specific limitation on the composition of the photosensitive silver halide available for the present invention, and examples of which include silver chloride, silver chlorobromide, silver bromide, silver iodobromide and silver iodochlorobromide. The halogen composition distribution within the silver halide grains may be uniform, or may change stepwise or continuously. Silver halide grains with a core/shell structure may also be used preferably.

Methods for preparing photosensitive silver halide are well known in the art, and, for example, the methods described in Research Disclosure, No. 17029 (June, 1978) and U.S. Pat. No. 3,700,458 may be applied.

An amount of addition of the photosensitive silver halide as expressed in an amount of silver per 1 m$^2$ of photosensitive material is preferably 0.03 to 0.6 g/m$^2$, more preferably 0.05 to 0.4 g/m$^2$, and still more preferably 0.1 to 0.4 g/m$^2$.

The binder used in the layer containing the fatty acid silver salt of the present invention may be an arbitrary polymer, and is transparent or semi-transparent, colorless in general, and can be made of natural polymer, synthetic resin, polymer and copolymer and other film-forming media. Examples thereof include gelatin, gum arabic, poly(vinyl alcohol), hydroxyethylcellulose, cellulose acetate, cellulose acetate butylate, poly(vinylpyrrolidone), casein, starch, poly (acrylic acid), poly(methyl methacrylate), poly(vinyl chloride), poly(methacrylic acid), copoly(styrene-maleic anhydride), copoly(styrene-acrylonitrile), copoly(styrene-butadiene), polyvinyl acetals [such as poly(vinylformal) and poly(vinylbutyral)], polyesters, polyurethanes, phenoxy resin, poly(vinylidene chloride), polyepoxides, polycarbonates, poly(vinyl acetate), cellulose esters and polyamides. The binder may also be formed by coating from water, organic solvent or emulsion.

An amount of the total binder of the image recording layer is preferably 0.2 to 30 g/m², and more preferably 1 to 15 g/m².

Other materials and compositions applicable to the thermally processed image forming material can be referred to JP-A-10-62899, JP-A-10-268465, JP-A-11-52509, JP-A-11-352625 to 352627, JP-A-11-349591, JP-A-12-7683, JP-A-12-72711, European Laid Open Patent Publication Nos. 0803764A1 and 0962812A1.

EXAMPLES

The present invention will be explained more specifically hereinafter by referring to the following Examples and examinations. The components, amounts of use thereof, ratios, operations and the like mentioned in the following Examples may properly be modified without departing from the spirit of the present invention. The scope of the present invention, therefore, is not limited to the specific Examples described below.

Compounds used in the Examples are shown below:

Spectral Sensitization Dye 1

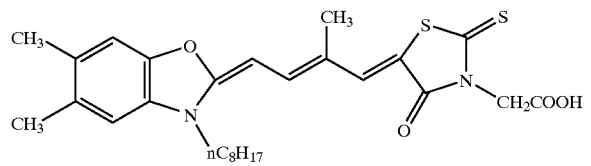

Tellurium Compound

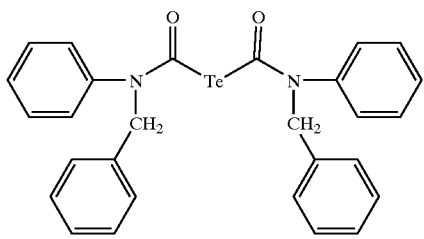

Surfactant "A"

$C_9H_{19}$—⟨⟩—O—$(CH_2CH_2O)_n$—H n ≈ 8.5

Basic Precursor Compound

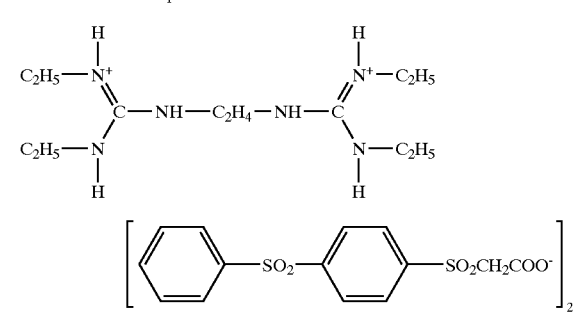

Cyanine Dye Compound

Blue Dye Compound

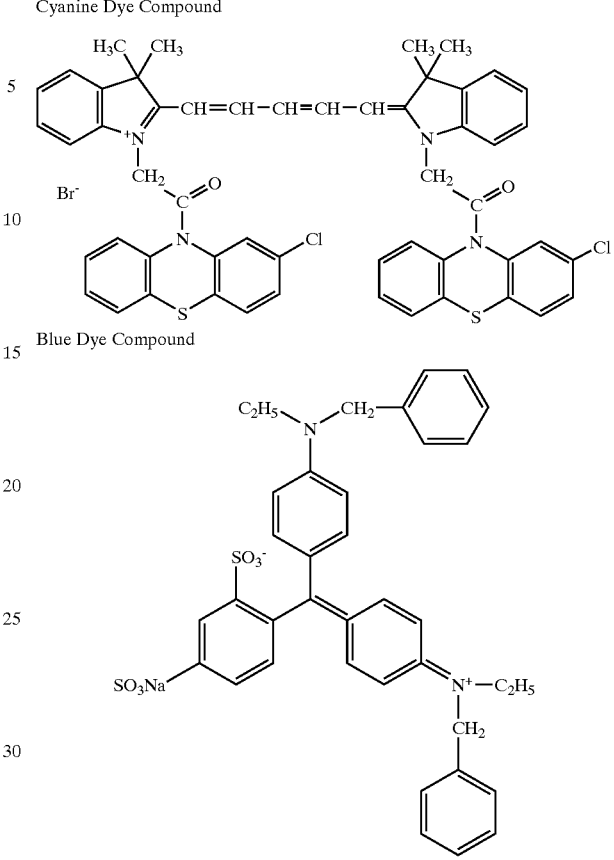

1. Fabrication of PET Support

PET with an intrinsic viscosity (IV) of 0.66 (measured in phenol/tetrachloroethane=6/4 (ratio by weight) at 25° C.) was obtained by the general procedures using terephthalic acid and ethylene glycol. The obtained PET was pelletized, dried at 130° C. for 4 hours, melted at 300° C., extruded from a T-die and rapidly cooled, to obtain a unstretched film so as to have a thickness after heat setting of 175 μm.

The film was then longitudinally stretched 3.3 times at 110° C. using rollers different in the peripheral speed and then transversely stretched 4.5 times at 130° C. using a tenter. Subsequently, the film was heat-set at 240° C. for 20 seconds, and then relaxed by 4% in the transverse direction at the same temperature. Thereafter, a portion chucked by the tenter was slit off and the film was knurled at the both edges and then taken up. Thus, a rolled support of 175 μm thick was fabricated.

2. Surface Corona Treatment

Using a solid state corona treatment apparatus (6-kVA model, product of Pillar Corporation), the both planes of the support were treated at 20 m/min under the room temperature. Referring to indicator values of current and voltage, it was confirmed that the support was treated at 0.375 kVA·minute/m². The treatment frequency was 9.6 kHz and the gap clearance between the electrode and dielectric roll was 1.6 mm.

3. Fabrication of Undercoated Support (Preparation of Undercoating Liquid "A")

To 200 ml of a 30 wt % water-base dispersion of polyester copolymer (PESRES IN A-515 GB, product of Takamatsu Oil & Fat Co., Ltd.), 1 g of polystyrene microgram (average particle size of 0.2 μm) and 20 ml of Surfactant "A" (1 wt %) were added, and the total volume was adjusted to 1,000 ml by adding distilled water, thereby to obtain the undercoating liquid "A".

(Preparation of Undercoating Liquid "B")

To 680 ml of distilled water, 200 ml of a 30 wt % water-base dispersion of styrene-butadiene copolymer [syrene/butadiene/itaconic acid=47/50/3 (weight ratio)], 0.1 g of polystyrene microgram (average grain size of 2.5 μm) were added, and the total volume was adjusted to 1,000 ml by adding distilled water, thereby to obtain the undercoating liquid "B".

(Preparation of Undercoating Liquid "C")

Ten grams of an inert gelatin was dissolved in 500 ml of distilled water, and thereto 40 g of a 40 wt % water-base dispersion of stannic oxide-antimony oxide complex microgram described in JP-A-61-20033 was added, and the total volume was adjusted to 1,000 ml by adding distilled water, thereby to obtain the undercoating liquid "C".

(Fabrication of Undercoated Support)

On one plane of the support already treated by the above-described corona discharge treatment, the undercoating liquid "A" was coated using a bar coater with a wet coated amount of 5 ml/m$^2$ and was allowed to dry at 180° C. for 5 minutes. The film thickness after the drying was approx. 0.3 μm. On the rear plane (back plane) of the support already treated by the above-described corona discharge treatment, the undercoating liquid "B" was coated using a bar coater with a wet coated amount of 5 ml/m$^2$ and then dried at 180° C. for 5 minutes to achieve a dry film thickness of 0.3 μm, and further thereon the undercoating liquid "C" was coated using a bar coater with a wet coated amount of 3 ml/m$^2$ and then dried at 180° C. for 5 minutes to achieve a dry film thickness of 0.03 μm. Thus an undercoated support was obtained.

4. Preparation of Dispersion of Fatty Acid Silver Salt Grains "A"

While stirring 876 g of behenic acid (Edenor C22-85R, product of Henkel Corporation), 4,230 ml of distilled water and 1,200 ml of tert-butanol at 75° C., added over 5 minutes was 492 ml of a 5N aqueous NaOH solution, and then reacted for 60 minutes to obtain sodium behenate solution. Independently, 2,062 ml of aqueous solution containing 404 g of silver nitrate (pH 4.0) was prepared and kept at 10° C. A reaction vessel containing 6,350 ml of distilled water and 300 ml of tert-butanol was kept at 30° C., and an entire volume of the aqueous silver nitrate solution was added at a constant flow rate over 60 minutes, and 7 minutes after, an entire volume of the sodium behenate solution was added at a constant flow rate over 62 minutes (the last 9-minute period was dedicated to the single addition of the sodium behenate solution). The mixture was allowed to stand for 20 minutes under stirring, and then cooled to 25° C. The solid content was separated by suction filtration, and then washed with water until electric conductivity of the filtered water decreased as low as 30 μS/cm. The obtained solid content was stored in a form of a wet cake without drying.

To 560 g of the obtained wet cake of the fatty acid silver (solid content=40%), 424 g of distilled water and 22 g of polyvinyl alcohol (PVA-205, product of Kuraray Co., Ltd.) were added, and the mixture was then preliminarily dispersed using T. K. Homodisper Model 2M-5 (product of Tokushu Kika Kogyo K.K.) at 5,000 rpm for 15 minutes. The obtained grain was found to have an average grain size of 5.36 μm.

The preliminarily dispersed solution was dispersed once using a dispersion apparatus (Micro Fluidizer M-110S-EH, manufactured by Micro Fluidex International Corporation, equipped with G10Z interaction chamber manufactured by Mizuho Kogyo K.K.) under a pressure of 1,600 kg/cm$^2$, to obtain the dispersion "A" of the fatty acid silver salt grains. Here the temperature control was effected so as to regulate an inlet temperature at 5° C., and outlet temperature at 30° C.

5. Preparation of Dispersion of Fatty Acid Silver Salt Grains "B"

Dispersion "B" was prepared using a small-sized crystallization equipment as shown in FIG. 4. While stirring in a tank 32 a mixture of 876 g of behenic acid (Edenor C22-85R, product of Henkel Corporation), 4,230 ml of distilled water and 1,200 ml of tert-butanol at 75° C., added thereto was 492 ml of a 5N aqueous NaOH solution over 5 minutes, and was then allowed to react for 60 minutes to obtain sodium behenate solution. Independently, 2,062 ml of aqueous solution containing 404 g of silver nitrate (pH 4.0) was prepared and kept in a tank 31 at 10° C.

While rotating a mixing blade of a closed mixing apparatus 38 (Pipeline Mixer Model LR-I, product of Mizuho Kogyo K.K.) at 10,000 rpm (a linear velocity at the vane tip=4.2 m/second, stirring power =5.5 kW/L), the above aqueous silver nitrate solution was fed at a constant flow rate of 29 ml/minute, and 5 seconds after, the sodium behenate solution was fed at a constant flow rate of 98 ml/minute, which were then sent via an heat exchanger 39 to a tank 40 and stocked. An average temperature of the content of the tank 40 was 35° C., when a cooling water of 10° C. was supplied to a jacket of the tank 40 at 20 L/minute while ceasing supply of cooling water to the heat exchanger 39. The mixture was allowed to stand for 20 minutes under stirring, and then cooled to 25° C. The solid content was separated by suction filtration, and then washed with water until electric conductivity of the filtered water decreased as low as 30 μS/cm. The obtained solid content was stored in a form of a wet cake without drying.

Successive processes for preparing the dispersion "B" of the fatty acid silver salt grains are similar to those for the dispersion "A".

6. Preparation of Dispersion of Fatty Acid Silver Salt Grains "C"

Dispersion "C" was prepared using the small-sized crystallization equipment as shown in FIG. 4. While stirring in the tank 32 a mixture of 876 g of behenic acid (Edenor C22-85R, product of Henkel Corporation), 4,230 ml of distilled water and 1,200 ml of tert-butanol at 75° C., added thereto was 492 ml of a 5N aqueous NaOH solution over 5 minutes, and was then allowed to react for 60 minutes to obtain sodium behenate solution. Independently, 2,062 ml of aqueous solution containing 404 g of silver nitrate (pH 4.0) was prepared and kept in a tank 31 at 10° C., and 6,000 ml of pure water was stored in a tank 41 at 10° C. While rotating a mixing blade of a closed mixing apparatus 38 (Pipeline Mixer Model LR-I, product of Mizuho Kogyo K.K.) at 10,000 rpm, the above aqueous silver nitrate solution and pure water were fed at constant flow rates of 29 ml/minute and 98 ml/minute, respectively, and 5 seconds after, the sodium behenate solution was fed at a constant flow rate of 98 ml/minute, which were then sent via an heat exchanger 39 to a tank 40 and stocked. An average temperature of the content of the tank 40 was 30° C., when a cooling water of 10° C. was supplied to a jacket of the tank 40 at 20 L/minute while ceasing supply of cooling water to the heat exchanger 39. The mixture was allowed to stand for 20 minutes under stirring, and then cooled to 25° C. The solid content was separated by suction filtration, and then washed with water until electric conductivity of the filtered water decreased as low as 30 μS/cm. The obtained solid content was stored in a form of a wet cake without drying.

Successive processes for preparing the dispersion "C" of the fatty acid silver salt grains are similar to those for the dispersion "A".

7. Preparation of Dispersion of Fatty Acid Silver Salt Grains "D"

Dispersion "D" was prepared similarly to the dispersion "C" except that 6,000 ml of a 4 vol % aqueous tert-butanol solution was stored in a tank 41 and fed at a constant flow rate of 98 ml/minute.

8. Preparation of Dispersion of Fatty Acid Silver Salt Grains "E"

Dispersion "E" was prepared similarly to the dispersion "C" except that 6,000 ml of a 1 wt % aqueous polyvinyl alcohol (PVA-205, product of Kuraray Co., Ltd.) solution was stored in a tank 41 and fed at a constant flow rate of 98 ml/minute.

9. Preparation of Dispersion of Fatty Acid Silver Salt Grains "F"

Dispersion "F" was prepared using the small-sized crystallization equipment as shown in FIG. 2. While stirring in the tank 12 a mixture of 876 g of behenic acid (Edenor C22-85R, product of Henkel Corporation), 4,230 ml of distilled water and 1,200 ml of tert-butanol at 75° C., added thereto was 492 ml of a 5N aqueous NaOH solution over 5 minutes, and was then allowed to react for 60 minutes to obtain sodium behenate solution. Independently, 2,062 ml of aqueous solution containing 404 g of silver nitrate (pH 4.0) was prepared and kept in a tank 11 at 10° C. The tank 20 was pre-charged with 6,000 ml of pure water, which was circulated at a flow rate of 1,000 ml/minute via the pump 17. While rotating a mixing blade of a closed mixing apparatus 18 (Pipeline Mixer Model LR-I, product of Mizuho Kogyo K.K.) at 10,000 rpm, the above aqueous silver nitrate solution was fed at a constant flow rate of 29 ml/minute, and 5 seconds after, the sodium behenate solution was fed at a constant flow rate of 98 ml/minute, which were then sent via an heat exchanger 19 to a tank 20 and stocked. An average temperature of the content of the tank 20 was 30° C., when a cooling water of 10° C. was supplied both to a jacket of the tank 20 and the heat exchanger 19 at 20 L/minute. The mixture was allowed to stand for 20 minutes under stirring, and then cooled to 25° C. The solid content was separated by suction filtration, and then washed with water until electric conductivity of the filtered water decreased as low as 30 μS/cm. The obtained solid content was stored in a form of a wet cake without drying.

Successive processes for preparing the dispersion "F" of the fatty acid silver salt grains are similar to those for the dispersion "A".

10. Preparation of Dispersion of Fatty Acid Silver Salt Grains "G"

Dispersion "G" was prepared similarly to the dispersion "B" except that a cooling water of 5° C. was fed to the heat exchanger 39, thereby to attain an average temperature of the content of the tank 40 of 30° C.

11. Preparation of Dispersion of Fatty Acid Silver Salt Grains "H"

Dispersion "H" was prepared similarly to the dispersion "F" except that a cooling water of 5° C. was fed to the heat exchanger 19, thereby to attain an average temperature of the content of the tank 20 of 25° C.

Conditions for the preparation of the dispersions "A" to "H" of the fatty acid silver salt grains were listed in Table 1. Average grain size of the fatty acid silver salt grains in the dispersions "A" to "H", coefficient of variation thereof, viscosity measured by a B-type viscometer, and rise in the filtration pressure (a difference between the initial pressure and final pressure after filtering 2 kg of the dispersion through Epocel filter EC of 1.5 cm diameter produced by PAUL, Ltd. at 50 ml/minute) were shown in Table 2.

TABLE 1

| Dispersion | Preparation method | Added liquid | | | Temp. of coolng water (° C.) | Temp. of content in the tank (° C.) |
|---|---|---|---|---|---|---|
| | | Component 1 | Component 2 | Component 3 | | |
| A (Comparison) | tank | aq. AgNO$_3$ | Na behenate solution | — | — | 35 |
| B (Invention) | closed mixing apparatus | aq. AgNO$_3$ | Na behenate solution | — | — | 35 |
| C (Invention) | closed mixing apparatus | aq. AgNO$_3$ | Na behenate solution | water | — | 30 |
| D (Invention) | closed mixing apparatus | aq. AgNO$_3$ | Na behenate solution | aq. t-BuOH soln. | — | 30 |
| E (Invention) | closed mixing apparatus | aq. AgNO$_3$ | Na behenate solution | aq. PVA soln. | — | 30 |
| F (Invention) | closed mixing apparatus | aq. AgNO$_3$ | Na behenate solution | obtained silver salt dispersion | — | 30 |
| G (Invention) | closed mixing apparatus | aq. AgNO$_3$ | Na behenate solution | — | 5 | 30 |
| H (Invention) | closed mixing apparatus | aq. AgNO$_3$ | Na behenate solution | obtained silver salt dispersion | 5 | 25 |

12. Preparation of 25 wt % Dispersion of Reducing Agent

Eighty grams of 1,1-bis(2-hydroxy-3,5-dimethylphenyl)-3,5, 5-trimethylhexane and 64 g of a 20 wt % aqueous solution of a modified polyvinyl alcohol (Poval MP-203, product of Kuraray Co., Ltd.) were added with 176 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0.5 mm and dispersed for 5 hours, thereby to obtain the dispersion of the reducing agent. Reducing agent grains contained in thus obtained dispersion were found to have an average grain size of 0.72 μm.

13. Preparation of 20 wt % Dispersion of Mercapto Compound

Sixty-four grams of 3-mercapto-4-phenyl-5-heptyl-1,2,4-triazole and 32 g of a 20 wt % aqueous solution of a modified polyvinyl alcohol (Poval MP-203, product of Kuraray Co., Ltd.) were added with 224 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0.5 mm and dispersed for 10 hours, thereby to obtain the dispersion of the mercapto compound. Mercapto compound grains contained in thus obtained dispersion were found to have an average grain size of 0.67 μm.

14. Preparation of 30 wt % Dispersion of Organic Polyhalogen Compound

Forty-eight grams of tribromomethylphenylsulfone, 48 g of 3-tribromomethylsulfonyl-4-phenyl-5-tridecyl-1,2,4-triazole and 48 g of a 20 wt % aqueous solution of a modified polyvinyl alcohol (Poval MP-203, product of Kuraray Co., Ltd.) were added with 224 g of water, and then mixed to prepare a slurry. The slurry was then transferred to a vessel of a dispersion apparatus (¼ G Sand Grinder Mill, product of Aimex, Ltd.) together with 800 g of zirconia bead with an average diameter of 0.5 mm and dispersed for 5 hours, thereby to obtain the dispersion of the organic polyhalogen compound. Organic polyhalogen compound grains contained in thus obtained dispersion were found to have an average grain size of 0.74 μm.

15. Preparation of Methanol Solution of Phthalazine Compound

Twenty-six grams of 6-isopropylphthalazine was dissolved in 100 ml of methanol and used.

16. Preparation of 20 wt % Dispersion of Pigment

Sixty-four grams of C.I. Pigment Blue 60 and 6.4 g of DEMOL-N (product of Kao Corporation) were added with 250 g of water, and then mixed to prepare a slurry. The slurry was then fed into a vessel of a dispersion apparatus (¼G Sand Grinder Mill, product of Aimex, Ltd.) together with 800 g of zirconia bead with an average diameter of 0.5 mm, and dispersed for 25 hours to obtain the pigment dispersion. Pigment grains contained in thus obtained dispersion were found to have an average diameter of 0.21 μm.

17. Preparation of Silver Halide Emulsion 1

To 1421 ml of distilled water, 6.7 ml of an 1 wt % potassium bromide solution was added, and 8.2 ml of an 1N nitric acid and 21.8 g of phthalized gelatin were further added. The obtained mixture was kept stirred in a titanium-coated stainless reaction vessel at a constant liquid temperature of 35° C., and was then added with an entire volume of solution "a1" obtained by dissolving 37.04 g of silver nitrate in distilled water and diluting it up to 159 ml, by the controlled double jet method at a constant flow rate over 1 minute while keeping pAg at 8.1. Solution "b1" obtained by dissolving 32.6 g of potassium bromide in water and diluting it up to 200 ml was also added by the controlled double jet method. After that, 30 ml of a 3.5 wt % aqueous hydrogen peroxide solution was added, and 336 ml of a 3 wt % aqueous solution of benzimidazole was further added. Solution "a1" was further diluted with distilled water to 317.5 ml to obtain solution "a2", and solution "b1" was further added with dipotassium hexachloroiridate so as to attain a final concentration thereof of $1 \times 10^{-4}$ mol per mol of silver and diluted with distilled water up to 400 ml, which is a doubled volume of "b1", thereby to obtain solution "b2". Again an entire volume of solution "a2" was added to the mixture by the controlled double jet method at a constant flow rate over 10 minutes while keeping pAg at 8.1. Solution "b2" was also added by the controlled double jet method. After that, the mixture was added with 50 ml of a 0.5% methanol solution of 2-mercapto-5-methylbenzimidazole, the pAg of which was raised to 7.5 with silver nitrate, the pH of which was then adjusted to 3.8 with an 1N sulfuric acid, stopped stirring, subjected to precipitation/desalting/washing processes, added with 3.5 g of deionized gelatin, the pH and pAg thereof were adjusted to 6.0 and 8.2, respectively, with an 1N sodium hydroxide, thereby to obtain the silver halide emulsion.

Grains in the resultant silver halide emulsion were found to be pure silver bromide grains with an average sphere-equivalent diameter of 0.031 μm and a sphere-equivalent coefficient of variation of 11%. Grain size and so forth were determined based on an average diameter of 1,000 grains under electron microscopic observation. Ratio of [100] plane of such grains was determined as 85% based on the method of Kubelka-Munk.

The above emulsion was then heated to 50° C. under stirring, added with 5 ml of a 0.5 wt % methanol solution of N,N'-dihydroxy-N", N"-diethylmelamine and 5 ml of a 3.5 wt % methanol solution of phenoxyethanol, and one minute after, sodium benzenethiosulfonate was added in an amount of $3 \times 10^{-5}$ mol per mol of silver. Two minutes after, the solid dispersion of Spectral Sensitization Dye 1 (aqueous gelatin solution) was added thereto in an amount of $5 \times 10^{-3}$ mol per mol of silver, and further 2 minutes after, Tellurium Compound was added in an amount of $5 \times 10^{-5}$ mol per mol of silver, which was followed by ripening for 50 minutes. Immediately before completion of the ripening, 2-mercapto-5-methylbenzimidazole was added in an amount of $1 \times 10^{-3}$ mol per mol of silver, then the temperature of which was lowered to complete the chemical ripening, thereby to obtain the silver halide emulsion 1.

18. Preparation of Silver Halide Emulsion 2

To 700 ml of water, 22 g of phthalized gelatin and 30 mg of potassium bromide were added, and after conditioned at pH 5.0 and 35° C., 159 ml of an aqueous solution containing 18.6 g of silver nitrate and 0.9 g of ammonium nitrate, and an aqueous solution containing potassium bromide and potassium iodide at a molar ratio of 92:8 were added by the controlled double jet method over 10 minutes while keeping the pAg at 7.7. Subsequently, 476 ml of an aqueous solution containing 55.4 g of silver nitrate and 2 g of ammonium nitrate, and an aqueous solution containing $1 \times 10^{-5}$ mol/L of dipotassium hexachloroiridate and 1 mol/L of potassium bromide were added by the controlled double jet method over 30 minutes while keeping the pAg at 7.7. Thereafter, 1 g of 4-hydroxy-6-methyl-1,3,3a,7-tetraza-indene was added to the mixture, and the pH of which was lowered to cause agglomerative precipitation thereby to effect desalting. Then 0.1 g of phenoxyethanol was added, conditioned at pH5.9 and pAg8.2, to obtain silver iodobromide grain (cubic grain having an 8 wt % iodine-containing core, an average iodine content of 2 wt %, an average grain size of 0.05 μm, a coefficient of variation of the projected area of 8% and an (100) plane ratio of 88%).

Thus obtained silver halide grain was heated to 60° C., added with 85 μmol/mol Ag of sodium thiosulfonate, 1.1×10$^{-5}$ mol of 2,3,4,5,6-pentafluorophenyldiphenylphosphine selenide, 1.5×10$^{-5}$ mol of Tellurium Compound, 3.5×10$^{-8}$ mol of chloroauric acid and 2.7×10$^{-4}$ mol of thiocyanic acid, ripened for 120 minutes, rapidly cooled to 40° C., added with 1×10$^{-4}$ mol of Spectral Sensitization Dye 1 and 5×10$^{-4}$ mol of 2-mercapto-5-methylbenzimidazole, and rapidly cooled to 30° C., thereby to obtain a silver halide emulsion 2.

19. Preparation of Coating Liquid for Emulsion Layer
[Coating Liquid No. 1]

To 103 g of the above-obtained fatty acid silver dispersion, 5 g of a 20 wt % aqueous solution of polyvinyl alcohol PVA-205 (product of Kuraray Co., Ltd.) was added, and the mixture was kept at 40° C., which was further added with 23.2 g of the above-obtained 25 wt % dispersion of the reducing agent, 4.8 g of a 5% aqueous dispersion of C.I. Pigment Blue 60, 10.7 g of the 30 wt % dispersion of the organic polyhalogen compound and 3.1 g of the 20 wt % dispersion of the mercapto compound. Thereafter, 106 g of a 40 wt % SBR latex solution purified by ultrafiltration and kept at 40° C. was added thereto and thoroughly stirred, then 6 ml of the methanol solution of the phthalazine compound was added to obtain fatty acid silver-containing liquids. Five grams of the silver halide emulsion 1 and 5 g of silver halide emulsion 2 were preliminarily mixed thoroughly, and then added to the above fatty acid silver-containing liquid using a static mixer immediately before the coating, which was then directly fed to a coating die so as to attain a coated silver amount of 1.4 g/m$^2$.

Viscosity of the coating liquid for the emulsion layer was measured using a B-type viscometer (manufactured by Tokyo Keiki K.K.) at 40° C., and was found to be 85 mPa·s.

Viscosities of the coating liquid measured under shearing velocities of 0.1, 1, 10, 100 and 1000 (1/second) at 25° C. using RFS Fluid Spectrometer (manufactured by Rheometrix Far East Inc.) were 1500, 220, 70, 40 and 20 mPa·s, respectively.

The above SBR latex purified by ultrafiltration was obtained by diluting ten times the SBR latex [-St(68)-Bu(29)-AA(3)-, numerals are for polymerization ratio] with distilled water, and by purifying the diluted product by filtration using an UF-purification module FS03-FC-FUY03A1 (product of Daicen Membrane-Systems Ltd.) until the ion conductivity of the filtered water dropped to 1.5 mS/cm. The resultant latex concentration was found to be 40 wt %. The latex solution thus obtained was found to have an average particle size of 0.1 μm at 45% concentration, an electric conductivity of 4.2 mS/cm, and pH of 8.2.

20. Preparation of Coating Liquid for Intermediate Layer on the Emulsion Plane
[Coating Liquid for Intermediate Layer]

A coating liquid for the intermediate layer was prepared by mixing 772 g of a 10 wt % aqueous solution of polyvinyl alcohol PVA-205 (product of Kuraray Co., Ltd.), 226 g of a 27.5 wt % solution of methyl methacrylate/styrene/2-ethylhexylacrylate/hydroxyethyl methacrylate/acrylic acid copolymer latex (copolymerization ratio by weight of 59/9/26/5/1), 2 ml of a 5 wt % aqueous solution of Aerosol OT (American Cyanamide Corporation), 4 g of benzyl alcohol, 1 g of 2,2,4-trimethyl-1,3-pentanediol monoisobutylate and 10 mg of benzoisothiazolinone, which was then fed to a coating die so as to attain a coating amount of 5 ml/m$^2$.

Viscosity of the coating liquid measured at 40° C. using a B-type viscometer was found to be 21 mPa·s.

21. Preparation of Coating Liquid for First Protective Layer on the Emulsion Plane
[Coating Liquid for First Protective Layer]

Eighty grams of inert gelatin was dissolved in water, and added thereto were 138 ml of a 10 wt % methanol solution of phthalic acid, 28 ml of an 1N sulfuric acid, 5 ml of a 5 wt % aqueous solution of Aerosol OT (American Cyanamide Corporation) and 1 g of phenoxyethanol, and was further added with water to adjust a total weight to 1,000 g, thereby to obtain a coating liquid, which was then fed to a coating die so as to attain a coating amount of 10 ml/m$^2$.

Viscosity of the coating liquid measured at 40° C. using a B-type viscometer was found to be 17 mPa·s.

22. Preparation of Coating Liquid for Second Protective Layer on the Emusion Plane
[Coating Liquid for Second Protective Layer]

One hundred grams of inert gelatin was dissolved in water, and added thereto were 20 ml of a 5 wt % aqueous solution of potassium N-perfluorooctylsulfonyl-N-propylalanine, 16 ml of a 5 wt % aqueous solution of Aerosol OT (American Cyanamide Corporation), 25 g of polymethyl methacrylate microgram (average grain size=4.0 μm), 44 ml of an 1N sulfuric acid, and 10 mg of benzoisothiazolinone, and was further added with water to adjust a total weight to 1,555 g. The mixture was added with 445 ml of an aqueous solution containing 4 wt % chrome alum and 0.67% of phthalic acid using a static mixer immediately before the coating, and was then fed to a coating die so as to attain a coating amount of 10 ml/m$^2$.

Viscosity of the coating liquid measured at 40° C. using a B-type viscometer was found to be 9 mPa·S.

23. Preparation of Coating Liquid for the Back Side
[Preparation of Solid Micrograin Dispersion of Basic Precursor Compound]

Sixty-four grams of Basic Precursor Compound, 10 g of surfactant DEMOL-N (product of KAO Corporation), and 246 ml of distilled water were mixed, and the mixture was bead-dispersed using a sand mill (¼-gallon Sand Grinder Mill manufactured by AIMEX Corporation) to obtain a solid microgram dispersion of the Basic Precursor Compound with an average particle size of 0.2 μm. [Preparation of Solid Micrograin Dispersion of Dye]

To 305 ml of distilled water, added were 9.6 g of the Cyanine Dye Compound and 5.8 g of sodium p-alkylbenzenesulfonate, and the mixture was then bead-dispersed using a sand mill (¼-gallon Sand Grinder Mill manufactured by AIMEX Corporation) to obtain a solid microgram dispersion of the Dye with an average particle size of 0.2 μm.

[Preparation of Coating Liquid for the Antihalation Layer]

Seventeen grams of gelatin, 9.6 g of polyacrylamide, 70 g of the above-described solid microgram dispersion of the Basic Precursor Compound, 56 g of the above-described solid microgram dispersion of the Dye, 1.5 g of polymethyl methacrylate micrograin(average particle size=6.5 μm), 2.2 g of sodium polyethylenesulfonate, 0.2 g of an 1% aqueous solution of Blue Dye Compound and 844 ml of water were mixed to prepare the coating liquid for the antihalation layer.
[Preparation of Coating Liquid for the Protective Layer]

While keeping the temperature of a vessel at 40° C., 50 g of gelatin, 0.2 g of sodium polystyrenesulfonate, 2.4 g of N,N'-ethylenebis(vinylsulfoneacetamide), 1 g of sodium t-octylphenoxyethoxyethanesulfonate, 30 mg of benzoisothiazolinone, 32 mg of $C_8F_{17}SO_3K$, 64 mg of $C_8F_{17}SO_2N(C_3H_7)(CH_2CH_2O)_4(CH_2)_4$—$SO_3Na$, and 950 ml of water were mixed to obtain a coating liquid for the protective layer.

24. Fabrication of Photothermographic Materials "A" to "H"

On the back side of the undercoated support, the coating liquid for the antihalation layer and the coating liquid for the back side protective layer were simultaneously coated in a stacked manner, so as to attain a coated amount of solid content of 0.04 g/m² for the former, and a coated amount of gelatin of 1 g/m² for the latter, respectively. The coated films were then dried to obtain a back layer for preventing halation. On the opposite side of the back side, an emulsion layer, an intermediate layer, a first protective layer and a second protective layer were formed in this order by the simultaneous multi-layer coating based on the slide hopper coating method, thereby to obtain samples of the photothermographic materials.

The coating was effected at a speed of 100 m/min while keeping a gap between the tip of the coating die and the support at 0.18 mm, and keeping a pressure in a reduced pressure chamber lower by 392 Pa than the atmospheric pressure. In a successive chilling zone, the coated liquid was cooled by flowing air with a dry-bulb temperature of 18° C. and a wet-bulb temperature of 12° C. at an average wind velocity of 7 m/sec for 30 seconds, and then further dried in a helical floating drying zone by blowing wind with a dry-bulb temperature of 30° C. and a wet-bulb temperature of 18° C. at a blow-out wind velocity from the slit of 20 m/sec for 200 seconds.

25. Evaluation of Photographic Properties

The photothermographic materials "A" to "H" thus fabricated were exposed with a Kr semiconductor laser sensitometer (maximum output=500 mW) at 647 nm from a direction off-angled by 8 degrees from the normal, then subjected to a processing (heat development) at 120° C. for 15 seconds, and the obtained image was measured with a densitometer. Results of the measurement were evaluated by a minimum density (Dmin) and sensitivity [an inverse of a ratio of exposure energies giving Dmin and (Dmin plus 1.0)]. The sensitivity and Dmin were expressed as relative values assuming characteristic values for the photosensitive material "A" as 100. It is understood that higher sensitivity and lower Dmin account for better image producing properties.

26. Evaluation of Forced Storability

The photothermographic materials "A" to "H" were cut into 30.5 cm×25.4 cm pieces, four corners of which were cut off by 0.5 cm, and were allowed to stand for a day under a condition of 25° C./50% RH. The pieces were then enclosed in two bags made of a moisture-proof material by tens, and the bags were then allowed to stand in an oven at 50° C. and in a refrigerator at 4° C., respectively. Individual photosensitive materials were then exposed and heat-developed in a similar manner as in the evaluation of the photographic property, where a density at a non-exposed area (Dmin) was assumed to represent fog value. Rate of increase in fog was calculated by the following equation, where smaller rate of increase in fog indicates better time-dependent storability:

Rate of increase in fog=[(fog in a hot-stored piece−fog in a cold-stored piece)/(maximum density of a hot-stored piece−fog in a cold-stored piece)]×100

The results en bloc were shown in Table 2.

TABLE 2

| Dispersion and Photosensitive Material Samples | Grain Size | | Viscosity (mPa·s) | Filtration Pressure Rise (kg/cm²) | Photographic Property | | Rate of Increase in fog |
|---|---|---|---|---|---|---|---|
| | Average (μm) | Coefficient of Variation (%) | | | Dmin | Sensitivity | |
| A (comparison) | 0.62 | 28 | 18 | 0.23 | 100 | 100 | 1.5 |
| B (invention) | 0.46 | 18 | 19 | 0.18 | 101 | 105 | 1.3 |
| C (invention) | 0.41 | 16 | 18 | 0.18 | 101 | 105 | 1.1 |
| D (invention) | 0.43 | 14 | 20 | 0.12 | 100 | 102 | 1.1 |
| E (invention) | 0.35 | 17 | 22 | 0.13 | 102 | 103 | 1.0 |
| F (invention) | 0.32 | 15 | 22 | 0.10 | 101 | 105 | 1.0 |
| G (invention) | 0.32 | 16 | 23 | 0.10 | 100 | 105 | 1.0 |
| H (invention) | 0.25 | 12 | 25 | 0.08 | 100 | 105 | 1.0 |

27. Comparison with Conventional Technology

As compared with dispersion "A" according to the conventional method in which the reaction liquids are fed into an open tank and stirred to be mixed, the dispersions "B" to "H" prepared according to the present invention were found to have in general smaller average grain sizes. While not adhering to any kind of theory, this may be because air bubbles cannot be entrained in the liquid and thus allowed was a low-temperature charging. Other excellent effects such as improved photographic activity and sensitivity were also obtained in the present invention since the atmosphere in which the reaction liquids were placed was strictly controlled. This successfully reduces a coating amount of the organic acid silver salt and allows a silver-saving formulation and designing.

28. Effects of Third Component

In the preparation of the dispersions "C" to "F", the third component other than silver nitrate and sodium behenate was varied. Adding such third component at low temperatures successfully reduced the average grain size and could further improve the rise in the filtration pressure and rate of increase in fog.

29. Effects of Heat Exchanger

In the preparation of the dispersions "G" and "H", a cold water of 5° C. was fed to the heat exchanger to further lower the temperature of reaction liquid immediately after the mixing. This resulted in a more smaller grain size and improved the rise in the filtration pressure and rate of increase in fog.

In conclusion, the present invention can provide the dispersion of the fatty acid silver salt grains excellent in dispersion stability and coating property. The photothermographic material composed therewith is excellent in fog-preventive property even after the storage, and also excellent in image stability and light transmissivity after the heat development.

What is claimed is:

1. An apparatus for preparing non-photosensitive fatty acid silver salt grains comprising;
   a first feed means for feeding a silver ion-containing solution, the solvent of which being water or a mixture of water and an organic solvent, to a closed mixing means;

second feed means for feeding a solution of a fatty acid alkali metal salt, the solvent of which being water, an organic solvent, or a mixture of water and an organic solvent, to the closed mixing means;

a third feed means for feeding water, or a mixture of water and an organic solvent to the closed mixing means; and the closed mixing means for mixing matters fed from the first feed means, the second feed means and the third feed means, and discharging a liquid containing non-photosensitive fatty acid silver salt grains, and wherein a cooling means is provided for cooling the liquid containing non-photosensitive fatty acid silver salt grains discharged from the closed mixing means.

2. An apparatus for preparing non-photosensitive fatty acid silver salt grains comprising;

a first feed means for feeding a silver ion-containing solution, the solvent of which being water or a mixture of water and an organic solvent, to a closed mixing means;

a second feed means for feeding a solution of a fatty acid alkali metal salt, the solvent of which being water, an organic solvent, or a mixture of water and an organic solvent, to the closed mixing means;

the closed mixing means for mixing matters fed from the first feed means, the second feed means and a third feed means, and discharging a liquid containing non-photosensitive fatty acid silver salt grains; and the third feed means for feeding at least a part of the liquid containing non-photosensitive fatty acid silver salt grains discharged from the closed mixing means back to said closed mixing means.

3. The apparatus for preparing non-photosensitive fatty acid silver salt grains as claimed in claim 2, wherein a cooling means for cooling the liquid containing non-photosensitive fatty acid silver salt grains discharged from the closed mixing means is additionally provided.

4. The apparatus for preparing non-photosensitive fatty acid silver salt grains as claimed in claim 2, wherein the closed mixing means is a mixing apparatus having a rotating blade in a closed vessel.

5. The apparatus for preparing non-photosensitive fatty acid silver salt grains as claimed in claim 4, wherein a linear velocity at an outermost periphery portion of the rotating blade is 1 to 50 m/second.

6. The apparatus for preparing non-photosensitive fatty acid silver salt grains as claimed in claim 4, wherein a stirring power of the mixing apparatus is 0.1 to 10 KW per liter of a reaction mixture.

* * * * *